(12) United States Patent
Nibhanipudi

(10) Patent No.: US 11,933,703 B1
(45) Date of Patent: Mar. 19, 2024

(54) METHOD OF PROVIDING OBJECTIVE EVIDENCE OF A PHYSICAL CONTACT

(71) Applicant: Kumara V. Nibhanipudi, Scarsdale, NY (US)

(72) Inventor: Kumara V. Nibhanipudi, Scarsdale, NY (US)

( * ) Notice: Subject to any disclaimer, the term of this patent is extended or adjusted under 35 U.S.C. 154(b) by 0 days.

(21) Appl. No.: 17/989,892

(22) Filed: Nov. 18, 2022

(51) Int. Cl.
| | |
|---|---|
| *A61B 1/00* | (2006.01) |
| *C12N 15/10* | (2006.01) |
| *G01N 1/30* | (2006.01) |
| *G01N 21/64* | (2006.01) |
| *G06Q 50/26* | (2012.01) |
| *A61B 5/1172* | (2016.01) |

(52) U.S. Cl.
CPC ........... *G01N 1/30* (2013.01); *C12N 15/1003* (2013.01); *G01N 21/6486* (2013.01); *G06Q 50/265* (2013.01); *A61B 5/1172* (2013.01); *G01N 2001/302* (2013.01)

(58) Field of Classification Search
None
See application file for complete search history.

(56) References Cited

U.S. PATENT DOCUMENTS

2018/0363054 A1* 12/2018 Lum .................... C12Q 1/6881

* cited by examiner

*Primary Examiner* — Jyoti Nagpaul
(74) *Attorney, Agent, or Firm* — MaxGoLaw PLLC

(57) ABSTRACT

A method of providing objective, forensic evidence as to whether an alleged contact occurred in order to forensically establish an alleged fondling or unwanted sexual touching includes receiving a sample that is an article of clothing or skin that is alleged to have been contacted by an accused perpetrator, identifying at least one location on the sample from which to test, developing biological trace evidence on the sample at the at least one identified location, and extracting the biological trace evidence to obtain a unique identifier of the biological trace evidence at the at least one identified location. The biological trace evidence may be a handprint, fingerprint, or biochemical residue obtained from the sample in a location on the sample that corresponds to a know position on the accuser's body.

12 Claims, 1 Drawing Sheet

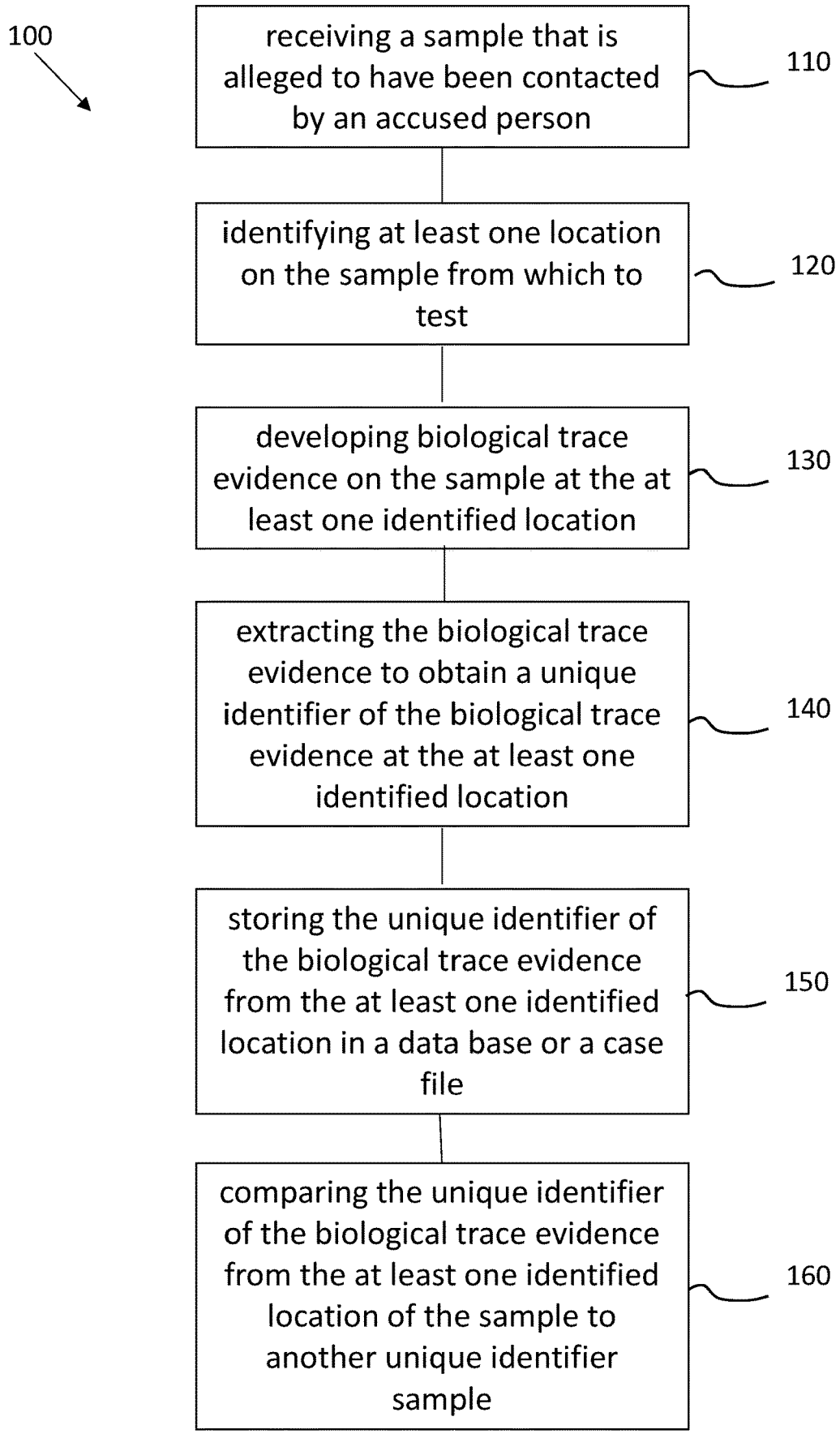

METHOD OF PROVIDING OBJECTIVE EVIDENCE OF A PHYSICAL CONTACT

FIELD OF THE INVENTION

The present invention relates to the field of evidence collection. More particularly, it relates to a method for determining the presence of and/or extracting and collecting biological trace evidence from an article of clothing or skin that is alleged to have been contacted by an accused perpetrator to provide objective, forensic evidence as to whether the alleged contact occurred.

BACKGROUND OF THE INVENTION

According to the National Sexual Violence Resource Center (NSVRC), in the United States, 81% of women and 43% of men report experiencing some form of sexual harassment and/or assault in their lifetime. Sexual assault is a legal term used to describe a wide range of sexual contact or behavior that occurs without explicit consent of the victim. Some forms of sexual assault include showing indecent images to another person, unwanted sexual touching or kissing, and rape.

While each form of sexual assault and each jurisdiction includes its own combination of elements that must be established in order to hold an accused perpetrator criminally liable for an alleged sexual assault, such as intent, consent, age of the victim, and surrounding circumstances, a baseline for proving such offenses is establishing that there was a contact between an accused perpetrator and the accuser. In instances or rape or attempted rape, there are several techniques available for collecting evidence including DNA and biological evidence from an accuser to provide forensic evidence of the unwanted contact underlying an alleged rape or attempted rape. Such techniques are typically known as "rape kits" and include collecting biological fluids by swabbing a victim's genitals, rectum, mouth and body surfaces to determine the presence of DNA of an accused perpetrator on the victim's body. The presence of DNA of an accused perpetrator on the victim's body thus provides objective forensic evidence of a sexual contact between the accused perpetrator and the victim.

However, in the case of unwanted physical contact, there is currently no way to forensically prove that the underlying alleged contact even occurred. Accordingly, proving such allegations can be extremely difficult, with the resulting legal cases often becoming a "he said, she said" battle of the witnesses, which can be traumatic for a victim. Given the difficulty in proving such claims, often times victims of an alleged unwanted physical contact chose to not report the crime. In such situations, the accused perpetrator is free from the consequences of their actions and is able to continue to be present in society and able to continue to perpetrate similar or worsening offenses on others. Similarly, an accused perpetrator, if innocent, lives under the weight of such an allegation.

Thus, there exists a need for a method for determining the presence of and/or extracting and collecting biological trace evidence from an article of clothing or skin that is alleged to have been contacted by an accused perpetrator to provide objective, forensic evidence as to whether the alleged contact occurred as a way to forensically establish an alleged unwanted physical contact.

SUMMARY OF THE INVENTION

The present invention provides a method of providing objective evidence of a physical contact, particularly as a method for determining the presence of and/or extracting and collecting biological trace evidence from an article of clothing or skin that is alleged to have been contacted by an accused perpetrator to provide objective, forensic evidence as to whether the alleged contact occurred in order to forensically establish an alleged unwanted physical contact. The method of providing objective evidence of a contact includes receiving a sample that is alleged to have been contacted by an accused perpetrator, identifying at least one location on the sample from which to test, developing biological trace evidence on the sample at the at least one identified location, and extracting the biological trace evidence to obtain a unique identifier of the biological trace evidence at the at least one identified location. The biological trace evidence may be a handprint, a fingerprint, or a biochemical residue from a person obtained from the sample in a location on the sample that corresponds to a known position on the accuser's body. The obtained unique identifier is DNA information or a small molecule emitted profile. The method may additionally include comparing the obtained unique identifier of the biological trace evidence from the at least one identified location of the sample to another DNA sample or small molecule emitted profile sample that is obtained either from the accused perpetrator or from a database of known DNA samples or known small molecule emitted profile samples.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 is a flowchart showing the steps for a method of providing objective evidence of a contact according to embodiments of the present disclosure.

DESCRIPTION OF THE INVENTION

The present invention has utility as a method of providing objective evidence of a contact, particularly as a method for extracting and collecting biological trace evidence from an article of clothing or skin that is alleged to have been contacted by an accused perpetrator to provide objective, forensic evidence as to whether the alleged contact occurred in order to forensically establish an unwanted physical contact, such as those occurring through a pattern of sexual harassment; or second, third, or fourth degree sexual assault.

The present invention is hereafter described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

According to inventive embodiments and as shown in FIG. 1, a method 100 of providing objective evidence of a contact underlying an alleged fondling or unwanted sexual touching includes receiving a sample that is alleged to have been contacted by an accused perpetrator at step 110. Next, the method includes identifying at least one location on the sample from which to test at step 120. Step 130 of the method includes developing biological trace evidence on the sample at the at least one identified location. Next, the method includes extracting the biological trace evidence to obtain a unique identifier of the biological trace evidence at the at least one identified location, as shown in step 140 of FIG. 1.

According to some inventive embodiments, the biological trace evidence is at least a portion of handprint or a fingerprint that was left on the sample material when the sample material was contacted. According to some inventive embodiments, the biological trace evidence is a biochemical residue from a person, such as sebum, an oily and slightly waxy substance found on the skin, or another form of bodily fluid containing odortype information. Notably, an odortype is a genetically determined body odor of an individual that is as unique as fingerprints. An individual's odortype is determined in part by genes in a genomic region called the major histocompatibility complex (MHC). Odortype information is transmitted through body fluids such as sweat and urine, which contain numerous airborne chemical molecules known as volatile organic compounds (VOCs), many of which give off an odor. Human bodies emit a wide array of VOCs, both odorous and non-odorous, from our bodies. The VOCs emitted from different areas of the human body vary with age, diet, sex, physiological status and possibly genetic background. Therefore, body odors can be considered as individual 'odor-fingerprints'. Body odors are a result of the combination of hundreds of emitted odorous VOCs that are originally secreted from various cells inside the body via metabolic pathways. The major sources of VOCs include breath, sweat, skin, urine, feces, and vaginal secretions. Blood is also an important source of body odors because some metabolically produced VOCs are secreted into blood and eventually emitted to the external environment via breath and/or sweat. VOCs emitted from the skin surface are mainly derived from sweat, a fluid secreted by the sweat glands and sebum, an oily substance secreted by the sebaceous glands. Although some of these VOCs result from internal hormonal or metabolic changes, many VOCs appear to be derived from symbiotic bacteria that live on the skin surface and metabolize and transform secreted compounds in sweat and sebum.

According to some inventive embodiments, the objective evidence provided using the inventive method is forensic evidence. This forensic evidence is obtained by scientific methods and is generally admissible in court. Forensic evidence often helps to establish the guilt or innocence of an accused perpetrator. Such forensic evidence may be used in an investigation and prosecution of civil as well as criminal proceedings. This forensic evidence can be used to corroborate an accuser's account of an unwanted contact by establishing that an accused perpetrator did in fact make a contact with the accuser.

According to some inventive embodiments, the sample utilized to perform the inventive method is an article of clothing, that includes but is not limited to cloth or fabric, or a portion of skin of an accuser that is alleged to have been contacted by an accused perpetrator. Notably, cloth or fabric articles of clothing and skin are porous carries. Typically, such porous carriers are quite difficult to extract biological trace evidence, such as handprints, palmprints, fingerprints, or biochemical residue from a person from given the discontinuous nature of the surface of such porous carries. For example, some porous carriers, such as fabrics, are made by crossing, sintering and connecting some fine flexible slender objects, and therefore, although the fingerprint can be developed on the fabric, the line in the fingerprint is not continuous after the fingerprint is enlarged, and many breakpoints appear. Therefore, comparing the fingerprint photo on the fabric with the fingerprints found in a database or obtained directly from an accused perpetrator, is not always reliable.

According to inventive embodiments, the sample is prepared by swabbing the skin of the accuser or by cutting off a portion of the article of clothing where the biological trace evidence is developed, and then performing the extracting step 140.

According to some inventive embodiments, the at least one location on the sample that is identified for testing corresponds to a known position on an accuser's body. That is, the at least one location on the sample that is identified for testing may be from a location on an article clothing that when worn by the accuser is positioned over the accuser's breast, chest, back, leg, arm, abdomen, or buttocks. Accordingly, the presence of DNA information on the sample in a location that corresponds to a position on the accuser's body such as breast, chest, back, leg, arm, abdomen, or buttocks that corroborates the alleged unwanted contact claim thus provides objective, forensic evidence that the underlying contact did in fact occur. Accordingly, this evidence makes it very difficult for the accused perpetrator to simply deny having made the alleged contact. Conversely, the absence of unique identifier information on the sample in a location that corresponds to a position on the accuser's body such as breast, chest, back, leg, arm, abdomen, or buttocks serves to contradict the alleged unwanted contact claim thus provides objective, forensic evidence that the underlying contact did in fact not occur.

According to some inventive embodiments, the step 130 of developing biological trace evidence on the sample at the at least one identified location and the step 140 of extracting the biological trace evidence to obtain a unique identifier of the biological trace evidence at the at least one identified location involves obtaining DNA evidence or a small molecule emitted profile, such as an odortype/odorprint described above based on VOCs emitted from an individual's body. According to some inventive embodiments, obtaining DNA as the unique identifier may be accomplished by carrying out the method disclosed in U.S. Pat. No. 10,996,171B2. According to some inventive embodiments, the step 130 of developing biological trace evidence on the sample at the at least one identified location includes using a biological fluorescent development reagent to process the sample so as to develop biological trace evidence on the sample. According to embodiments, the raw material formulation of the biological fluorescent development reagent is, in percent by weight: 0.01%-0.5% of indanedione, 4%-10% of ethyl acetate, 0.5%-1.5% of glycerol, 5%-15.5% of pure alcohol, and 73.5%-90% of petroleum ether. According to some inventive embodiments in which the unique identifier is a small molecule emitted profile, Gas chromatography (GC) and gas chromatography, mass spectrometry (GC-MS), and/or G-C-MS-olfactometer (GC-MS-O) are used to separate and identify VOCs and to examine mass spectra and odor qualities of individual GC-separated odorants simultaneously. Using the GC-MS-O, characteristic odorous compounds unique to a given individual can then be identified.

According to further embodiments, the step 130 of developing biological trace evidence additionally includes immersing the sample in the biological fluorescent development reagent or spraying the biological fluorescent development reagent on the sample at the at least one identified location and then drying the sample in an environment having a relative humidity of less than 40% at a temperature of 50° C.-120° C. Next, the step includes irradiating the dried sample with a laser having a wavelength of 532 nm and a full width at half-maximum of less than 1 nm, controlling a surface of the sample with an illuminance of over 300,000 lux, and using a cut-off filter under 540 nm to develop the biological trace evidence on the sample.

According to some inventive embodiments, before immersing in the biological fluorescent development reagent or spraying the biological fluorescent development reagent, a moisture content of the sample is controlled to be 6-7%. According to some inventive embodiments, when immersing the sample in the biological fluorescent development reagent, immersing time is controlled to be 5-10 sec. According to some inventive embodiments, the sample wetted by biological the fluorescent development reagent is subsequently dried in an environment having a relative humidity of less than 30% at a temperature of 50° C.-90° C.

In the present implementations, a cut-off filter under 540 nm refers to a cut-off filter that allows only light waves of or above 540 nm to pass through, and other light waves cannot pass. In the present disclosure, pure alcohol means >99.7% absolute ethanol, $C_2H_5OH$.

Preferably, a method for preparing the biological fluorescent development reagent comprises following steps:
(a) dissolving glycerin in pure alcohol to obtain a solution 1;
(b) dissolving indanedione in ethyl acetate to obtain a solution 2;
(c) mixing the solution 1 obtained in the step (a) and the solution 2 obtained in the step (b), adding petroleum ether, and uniformly stirring the mixture to give the biological fluorescent development reagent.

According to some inventive embodiments, the method 100 additionally includes storing the unique identifier of the biological trace evidence from the at least one identified location in a data base or a case file, as shown at step 150.

According to some inventive embodiments, the method 100 additionally includes comparing the unique identifier of the biological trace evidence from the at least one identified location of the sample to another sample, as shown at step 160 of FIG. 1. According to embodiments, the other sample for the comparison at step 160 is obtained from the accused perpetrator. According to other embodiments, the other sample is provided from a database of DNA or small molecule emitted profile samples, thereby allowing for comparison even in situations where the identity of the accused perpetrator is unknown to the accuser.

Fingerprint and DNA profile storage for millions of humans in the United States are known from state, local and federal government as well as private sources, for example, the fingerprint and DNA profile data stored by the U.S. Department of Justice, Federal Bureau of Investigation. Biometric data, potentially including odorprints, are collected by Interpol and other international and domestic agencies as well for those who may be suspected, convicted and/or imprisoned for terrorist or criminal activity. Fingerprints are often voluntarily collected by state agencies at a child's birth for purposes of possible future use in the event of a kidnapping, victim identification or other reason for which parents voluntarily permit the collection and storage of their children's fingerprints and other biometric data in databases. Automatic fingerprint identification services (AFIS) are known whereby a set of prints may be automatically collected, digitally stored and compared for identification purposes at local police departments.

The collected unique identifier information may be physically returned or transmitted to a central location where software may be run, for example, to resolve a DNA mixture per U.S. Pat. No. 7,162,372 or 7,672,789, (In particular, the University of Tennessee offers mixture deconvolution to police and fire and rescue organizations.) Peak fitting algorithms analyze two dimensional graphic data representing DNA profile peaks and perform allele peak fitting and attribute extraction, for example, per US Published Application No. 2009/022845 of Sep. 10, 2008, (now U.S. Pat. No. 8,645,073 issued Feb. 4, 2013). Similar peak analyses may be conducted from results of Gas chromatography (OC) and gas chromatography, mass spectrometry (GC-MS), and/or GC-MS-olfactorneter (GC-SIS-O).

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention but is not meant to be a limitation upon the practice thereof. The following claims, including all equivalents thereof, are intended to define the scope of the invention.

The invention claimed is:
1. A method of providing objective evidence of a contact underlying an alleged fondling or unwanted sexual touching, the method comprising:
receiving a sample of an article of clothing that is alleged to have been contacted by an accused perpetrator, said sample of clothing worn by the accuser during the contact by the accused perpetrator;

identifying at least one location on the sample from which to test, the at least one location on the sample corresponding to a position on an accuser's body where the alleged fondling or unwanted sexual touching occurred;

developing biological trace evidence on the sample at the at least one identified location, wherein the biological trace evidence is at least a portion of a handprint or a fingerprint, that includes sebum, an oily and slightly waxy substance found on skin; and extracting the biological trace evidence to obtain a unique identifier of the biological trace evidence at the at least one identified location.

2. The method of claim 1 wherein the objective evidence is forensic evidence.

3. The method of claim 1 wherein the sample further comprises a portion of skin of an accuser obtained from said article of clothing.

4. The method of claim 1 wherein developing biological trace evidence includes using a biological fluorescent development reagent to process the sample so as to develop biological trace evidence on the sample.

5. The method of claim 4 wherein a raw material formulation of the biological fluorescent development reagent is, in percent by weight: 0.01%-0.5% of indanedione, 4%-10% of ethyl acetate, 0.5%-1.5% of glycerol, 5%-15.5% of pure alcohol, and 73.5%-90% of petroleum ether.

6. The method of claim 4 wherein developing biological trace evidence additionally includes:

immersing the sample in the biological fluorescent development reagent or spraying the biological fluorescent development reagent on the sample at the at least one identified location;

drying the sample in an environment having a relative humidity of less than 40% at a temperature of 50° C.-120° C.;

irradiating the dried sample with a laser having a wavelength of 532 nm and a full width at half-maximum of less than 1 nm;

controlling a surface of the sample with an illuminance of over 300,000 lux; and using a cut-off filter under 540 nm to develop the biological trace evidence on the sample.

7. The method of claim 1 further comprising storing the Unique identifier in a database.

8. The method of claim 1 further comprising adding the unique identifier to a case file.

9. The method of claim 1 further comprising obtaining a DNA sample or a small molecule emitted profile from the accused perpetrator.

10. The method of claim 9 further comprising comparing the unique identifier to the DNA sample or small molecule emitted profile from the accused perpetrator.

11. The method of claim 1 further comprising comparing the unique identifier with DNA information or small molecule emitted profile in a database.

12. The method of claim 1 wherein the biological trace evidence obtained from said article of clothing further includes a biochemical residue from a person, a small molecule emitted profile, or another form of bodily fluid containing odortype information based on volatile organic compounds (VOC).

* * * * *